United States Patent [19]

Payne

[11] Patent Number: 5,055,621

[45] Date of Patent: Oct. 8, 1991

[54] RELATING TO ALDOL CONDENSATION

[75] Inventor: Laurence S. Payne, South Wilesborough, Great Britain

[73] Assignee: Unilever Patent Holdings B.V., Rotterdam, Netherlands

[21] Appl. No.: 507,223

[22] Filed: Apr. 11, 1990

[30] Foreign Application Priority Data

Apr. 11, 1989 [GB] United Kingdom ............... 8908104

[51] Int. Cl.$^5$ ...................... C07C 45/00; C07C 45/45
[52] U.S. Cl. ...................................... 568/433; 568/426
[58] Field of Search ........................ 568/433, 431, 426

[56] References Cited

U.S. PATENT DOCUMENTS 1,716,822  6/1929  Knorr et al.

FOREIGN PATENT DOCUMENTS

| 2637428 | 2/1978 | Fed. Rep. of Germany |
|---|---|---|
| 10540 | 3/1971 | Japan ............... 568/433 |
| 252442 | 12/1985 | Japan ............... 568/433 |

OTHER PUBLICATIONS

Chemical Abstracts, vol. 75, p. 459, (1971), abstract No. 35424s.

Chemical Abstracts, vol. 102, p. 621, (1987), abstract No. 213542t.

*Primary Examiner*—Werren B. Lone
*Attorney, Agent, or Firm*—Cushman, Darby & Cushman

[57] ABSTRACT

α-cinnamic aldehydes especially amyl and hexyl cinnamic aldehydes, are prepared by aldol condensation using a glycol solvent especially diethylene glycol.

15 Claims, No Drawings

RELATING TO ALDOL CONDENSATION

This invention relates to the preparation of α-substituted cinnamic aldehydes by aldol condensation and in particular the preparation of hexyl cinnamic aldehyde and amyl cinnamic aldehyde.

Hexyl cinnamic aldehyde is a traditional perfumery material and may be obtained by the condensation of octanal with benzaldehyde. This aldol condensation is carried out in the presence of alkali as catalyst, octanal being added slowly to the reaction mixture at moderate temperatures, generally from 30° to 50° C., in an amount somewhat less than equimolar. This is usually a heterogeneous aldol condensation for example in methanol as solvent, the reaction mixture is readily to be seen as a two-phase system.

A difficulty with aldol condensation reactions is that both starting materials undergo side reactions which in this case reduce the yield of hexyl cinnamic aldehyde and form troublesome by-products; the reaction of octanal with itself to form hexyldecenal is particularly serious in the production of perfumery quality product, this by-product being malodourous and not readily separable from the desired product. Its formation may be inhibited to some extent by maintaining a very low concentration of octanal relative to benzaldehyde in the reaction mixture, requiring long addition times in batch reactions and rendering impractical the use of plug-flow continuous reactors.

Further by-product formation results from the limited stability of benzaldehyde under the reaction conditions in which it tends to disproportionate via the Cannizzaro reaction to yield benzyl alcohol and benzoic acid, forming benzoate by further reaction with the alkali catalyst and having the effect of destroying both reactant and catalyst. Hexyl cinnamic aldehyde is destroyed by further aldol condensation with octanal and an effective excess of benzaldehyde is necessary to suppress this side-reaction.

The present invention proposes an improved process for the preparation of α-substituted cinnamic aldehydes by aldol condensation for example in the reaction of octanal with benzaldehye, in the presence of an alkali catalyst which is carried out in a solvent constituting the reaction phase and comprising a glycol alcohol in which the alkali catalyst is soluble.

The process of the present invention is carried out using as solvent a glycol, from which water may be readily removed for the purpose of recycling the solvent. Preferably the solvent is selected to provide substantially greater solubility for benzaldehyde than for hexyl cinnamic aldehyde, in order to suppress the further reaction of the latter. Optionally non-polar organic solvent, eg. hydrocarbon such as hexane may be added to further enhance this solubility difference. The process of the present invention may be carried out in a batch reactor or a steady state system such as a continuous stirred tank reactor. For the latter purpose diethylene glycol is preferred. Other glycols suitable for use in the present invention include ethylene glycol, propylene glycol, and dipropylene glycol. Mixtures of such glycols with limited amounts of water may be suitable; diethylene glycol for example may tolerate up to 20% water. Greater amounts of water than this are less desirable and preferably the solvent contains at most approximately 5% water.

It is also preferred in the present invention to use as catalyst potassium hydroxide, but other alkalis which are sufficiently soluble in the glycol solvent eg. sodium hydroxide, may also be used. The catalyst amount is preferably from 2 to 15% by weight of the solvent glycol/water mixture.

The reaction is preferably carried out at a temperature in the region of 40° C, but other temperatures may be used for example from 20° to 60° C.

An important advantage of the present invention is that the product is only slightly soluble in the glycol and therefore readily separable from alkali catalyst, concentrated in the glycol phase. Further, the glycol solvent may be recovered without itself being distilled for example water can be removed from recovered solvent by falling film methods, whereupon the solvent can be recycled.

The crude hexyl cinnamic aldehyde product must be washed to remove salts and traces of catalyst before recovery of refined product by distillation. The crude product is preferably washed for this purpose with strongly alkaline wash solutions eg. saturated sodium carbonate or less preferably, 5% sodium hydroxide For the purpose of recovering hexyl cinnamic aldehyde of perfumery quality, preferably distillation is carried out on a short-path still at temperatures below 160° C. and topping the distillate in a packed distillation column, if necessary followed by a further fractionation on a short-path still as before.

EXAMPLE 1

A solution of 21 gms of potassium hydroxide in 16 gms of water was mixed with 190 gms of diethylene glycol and charged to a 1 litre 3 neck flask fitted with a mechanically driven stirrer 2 inches in diameter, reflux condenser, nitrogen inlet and liquid feed inlet provided down the stirrer shaft from a peristaltic pump. The flask was maintained at 45° C. in a water bath and the stirrer speed set to 500 rpm. 150 gms (1.415 mole) benzaldehyde was added to the slurry in the reactor 128 gms of octanal (1.0 mole) was fed into the flask for a period of 4 hours. Stirring was continued thereafter for another 25 minutes and the reaction quenched by the addition of 250 gms of water.

The reaction mixture was allowed to settle, forming a lower aqueous phase of 569 gms which was extracted with two batches of 150 mls each of hexane These wash batches were combined, washed with 150 mls of saturated sodium carbonate and the hexane solution separated and dried over magnesium sulphate, filtered and the hexane removed by distillation, yielding 242.6 gms of crude hexyl cinnamic aldehyde. An analysis by GLC showed that the crude product contained 79.3% by weight of hexyl cinnamic aldehyde, 13.2% benzaldehyde, 2% benzyl alcohol and 1.3% hexyldecenal, representing a yield of 89.1% hexyl cinnamyl aldehyde based on octanal, the amount of benzaldehyde converted being 80.1%.

The crude hexyl cinnamic aldehyde was stabilised with 0.1% butylated hydroxytoluene and 0.4% diphenylamine and was stirred vigorously and distilled up a column 18 cm in length packed with Knitmesh. Benzaldehyde was recovered at 105° to 110° C. at 100 millibars. Pressure was reduced to 1.0 millibars, when an intermediate fraction of boiling point 50° to 112° C. was recovered, followed by the hexyl cinnamic aldehyde product of boiling point 112° C. at 1.0 millibars, amounting to a yield of 62.5% of the crude product.

This was refractionated in a 45 cm Knitmesh-packed column at 2 millibars pressure, reflux commencing at 118° C., to remove a head fraction amounting to approximately 4½% of the charge, leaving a topped hexyl cinnamic aldehyde product which was 98.3% pure and containing only 0.4% hexyldecenal was of acceptable perfumery quality.

EXAMPLE 2

Sodium hydroxide (18.9 g, 92.2% pure, 0.44 mol) was dissolved in water (31.5 g) and diethylene glycol (629 g, 563.6 ml) in a 2 l three-necked round-bottomed flask, fitted with a dropping funnel, stirrer and reflux condenser. Sodium benzoate (72 g., 0.5 mol.) was added to saturate the catalyst layer, followed by hexane (449 ml) and benzaldehyde (143 g, 1.35 mol) and then, whilst stirring under a blanket of nitrogen, octanal (177.2 g, 64% pure, 0.9 mol) was added over 6 h. at a temperature of 30°-35° C. The contents of the flask were then transferred to a separatory funnel. The upper hexane layer was removed and the diethylene glycol phase was further extracted with hexane (2×250 ml). The combined hexane solution was washed successively with sodium carbonate solution (saturated aqueous, 250 ml), hydrochloric acid solution (2% w/w aqueous, 250 ml) and saturated brine solution (250 ml). The organics were dried over anhydrous magnesium sulphate, and the solvent was removed under vacuum to give the crude product (280.7 g). Quantitative analysis (by glc internal standard (DMP) on an FFAP column, 100° C. isothermal for 25 min., then 40° C./min up to 200° C.) gave 59.8% ww. hexyl cinnamic aldehyde (168 g), which corresponds to a chemical yield of 86.3%. The same glc. analysis gave 11.1 %ww. recovered benzaldehyde (28.9 g) so that the benzaldehyde consumed in this experiment was 112.3 g. The crude product also contained unreacted octanal and hexyldecenal.

The diethylene glycol layer was then heated at 50° C. and 15 mm Hg pressure for 1 h., cooled and filtered to give the dehydrated solution (681.7 g). A sample of this recovered catalyst solution was titrated potentiometrically against 0.5 M hydrochloric acid. This analysis gave 2.08% ww. sodium hydroxide (14.2 g) and 11.1 %ww. sodium benzoate (75.9 g). The recovered catalyst phase was restored to its original composition by adding sodium hydroxide (3.25 g.), water (7.0 g.) and diethylene glycol (20 g.) for re-use in the next experiment of the series.

The results for the complete series are tabulated below:

| Experiment | Yield (g.) H.C.A. | Consumption (g.) Digol | NaOH | PhCHO |
|---|---|---|---|---|
| Initial | 170 | 20.0 | 3.2 | 112.3 |
| Reuse 1 | 168 | 14.5 | 2.5 | 116.0 |
| Reuse 2 | 169 | 20.0 | 2.9 | 112.8 |
| Reuse 3 | 160 | 22.6 | 3.2 | 113.6 |
| Reuse 4 | 180 | 19.3 | 4.0 | 118.5 |
| Reuse 5 | 179 | 20.0 | 4.5 | 119.6 |
| Reuse 6 | 190 | 32.0 | 4.2 | 123.3 |
| Reuse 7 | 189 | 38.0 | 4.1 | 124.4 |
| Reuse 8 | 183 | 31.0 | 4.5 | 121.4 |
| Total | 1588 | 217.4 | 33.1 | 1061.9 |

NOTE:
From Reuse 4, the same weight of 67% ww. octanal was used.

EXAMPLE 3

A catalyst phase was prepared comprising a dispersion in diethylene glycol of 9% of water and 4% sodium hydroxide previously dissolved.

An organic phase was prepared comprising a solution in hexane of 12% of octanal by weight of the solution and a 1.8 molar excess of benzaldehyde on the octanal.

A reactor vessel heated to 40° C. and maintained with a nitrogen blanket was charged with catalyst and organic phases from a previous experiment in a phase ratio catalyst organic of 0.6:1. It was equipped with computer-controlled stirrer and pump means for delivering the prepared phase supplies from balances to the vessel and discharging from it to a receiver vessel on a third balance. Balance determinations were also input to computer control.

Operations were started under computer control providing a residence time of 9½ hours and continuous stirring at 450 rpm. A 20 ml sample was then collected in the output receiver and its phase ratio determined by computer from the volumes of total sample and separated catalyst phase. The delivery rate of the prepared catalyst phase was then adjusted by the computer from these data, to maintain the initial phase ratio in the reactor. Further computer inputs were made from several more samples until the phase ratio of the output mixture was constant at 0.36. The density of the two phases separating from a larger sample was then measured and the ratio of the densities of the two phases was supplied to the computer to provide a more accurate control of the flow rates of the prepared phases.

The output mixture from the reactor was discarded for 28¼ hours to achieve steady state conditions. The output mixture for the next 17 hours was then collected. The lower catalyst phase was run-off and analysed, showing a concentration of 2.37% benzaldehyde. The upper organic phase was washed with saturated sodium carbonate solution, dried over anhydrous magnesium sulphate and the solvent removed under reduced pressure to give a crude hexyl cinnamic aldehyde product with the following analysis:

|  | % |
|---|---|
| Octanal | 0.57 |
| Octanal dimer | 0.30 |
| Benzaldehyde | 24.95 |
| Hexy cinnamic aldehyde | 72.5 |

The yield of aldehyde product was 90.7% w/w % based on octanal input and 87.4% w/w based on benzaldehyde reacted.

The crude product was refined as previously described.

EXAMPLE 4

A solution of 21 g of potassium hydroxide in 16 g of water was mixed with 190 g of ethylene glycol and charged to a 1 litre 3 neck flask fitted with a mechanically driven stirrer 2 inches in diameter, a distillation column, a nitrogen inlet and a liquid feed inlet provided from a peristaltic pump. The flask was maintained at 32° C. in a water bath and the stirrer speed set to 1000 rpm. 150 g (1.415 mole) benzaldehyde was added to the slurry in the reactor. 128 g of octanal (1.0 mole) was fed into the flask within a period of 4 hours. Stirring was continued thereafter for another 15 minutes and the reaction neutralised by the addition of 28 g of 85% phosphoric acid.

The nitrogen supply was then removed and excess benzaldehyde recovered at reduced pressure (bp. approx 80° C. at 25 millibars). The diethylene glycol was then recovered by fractional distillation at a reduced pressure (bp. approx 115° C. at 10 millibars). This allowed approximately 90% w/w of the glycol to be recycled.

The flask contents were then cooled to 40° C. and were worked up as in the previous examples. 211.2 g of crude hexyl cinnamic aldehyde was obtained with a purity of 95.0%. The yield based on octanal was 92.9%. The crude product was further purified as previously described.

I claim:

1. In a process for preparing an α-substituted cinnamic aldehyde by aldol condensation of an aldehyde in a solvent and in the presence of alkali as condensation catalyst, the improvement which comprises using, as the solvent, a glycol in which the alkali catalyst is soluble.

2. Process according to claim 1 in which the solvent comprises propylene glycol or dipropylene glycol.

3. Process according to claim 1 wherein the solvent comprises diethylene glycol.

4. Process according to claim 1 wherein the solvent further comprises up to 20% of water.

5. Process according to claim 4 wherein the solvent comprises approximately 5% water.

6. Process according to claim 1 wherein the catalyst concentration is from 2 to 15%.

7. Process according to claim 1 wherein the reaction is carried out at a temperature from 20° to 60° C.

8. Process according to claim 1 wherein the reaction is carried our in the additional presence of a non-polar solvent substantially immiscible with the glycol.

9. Process according to claim 8 wherein the non-polar solvent comprises a hydrocarbon.

10. Process according to claim 9 wherein the non-polar solvent comprises hexane.

11. Process according to claim 1 wherein the reactants comprise heptanal or octanal and benzaldehyde.

12. Process according to claim 1 wherein the glycol is recovered, dried and recycled to the process.

13. A continuous process according to claim 12 wherein the reactant aldehydes and glycol containing alkaline catalyst are separately delivered to the reaction phase from which glycol is recovered, dried and recycled to the process.

14. The process of claim 1 wherein the cinnamic aldehyde is an α-alkyl substituted cinnamic aldehyde and the glycol is one in which the benzaldehyde is more soluble than the cinnamic aldehyde.

15. The process of claim 14 wherein the reaction temperature is 20° to 60° C., the reactants are heptanal or octanal and benzaldehyde, the cinnamic aldehyde is hexyl or amyl cinnamic aldehyde and the glycol is diethylene glycol.

* * * * *